(12) United States Patent
Heideman et al.

(10) Patent No.: US 6,618,536 B1
(45) Date of Patent: Sep. 9, 2003

(54) INTEGRATED OPTICAL WAVEGUIDE SYSTEM

(75) Inventors: Rene Gerrit Heideman, Hengelo (NL); Jan Teunis Jan Ikkink, Eindhoven (NL); Paul Vincent Lambeck, Enschede (NL)

(73) Assignee: Mierij Meteo B.V. (NL)

( * ) Notice: Subject to any disclaimer, the term of this patent is extended or adjusted under 35 U.S.C. 154(b) by 0 days.

(21) Appl. No.: 09/446,027

(22) PCT Filed: Jun. 15, 1998

(86) PCT No.: PCT/EP98/03725

§ 371 (c)(1), (2), (4) Date: Apr. 4, 2000

(87) PCT Pub. No.: WO98/58285

PCT Pub. Date: Dec. 23, 1998

(30) Foreign Application Priority Data

Jun. 16, 1997 (NL) .............................................. 1006323

(51) Int. Cl.[7] ................................................. G02B 6/10
(52) U.S. Cl. ............................. 385/132; 385/2; 356/481
(58) Field of Search ............................. 385/16, 18, 130, 385/131, 132, 28, 29, 1, 2; 359/245, 248

(56) References Cited

U.S. PATENT DOCUMENTS 5,396,363 A * 3/1995 Valette ........................ 359/248

FOREIGN PATENT DOCUMENTS

EP          0539298      *  4/1993

OTHER PUBLICATIONS

Kiminori, Itoh et al. "Optical Waveguides for Surface Spectroscopy: FePO4 Thin–Film/K+–Doped Glass Composite Optical Waveguide Systems Having Tapered Velocity Couplers", Journal of Applied Physics, vol. 69, No. 11 (Jun. 1, 1991), pp.7425–7429.*

De Ridder, R.M. et al. "A Spot–Size Transformer for Fiber–Chip Coupling in Sensor Applications at 633 nm in Silicon Oxynitride", IEEE Lasers and Electro–Optics Society 1995 Annual Meeting, Oct. 30–31, 1995, vol. 2 (Nov. 1, 1995), pp. 86–87.*

Goodwill, D.J. et al. "Polymer Tapered Waveguides and Flip–Chip solder bonding as compatible technologies for efficient OEIC coupling", 1997 Proceedings 47th Electronic Components and Technology Conference, San Jose, CA May 18–21, 1997, pp. 788–796.*

Heideman, R.G. et al. "Fabrication and Packaging of Integrated Chemo–Optical Sensors," Sensors and Actuators B, vol. 35, No. 1 (Sep. 1996), pp.234–243.*

Heideman, R.G. et al. "Simple and Reuseable Fiber–to–Chip Interconnect with Adjustable Coupling Efficiency," Proceedings of the SPIE–The International Society for Optical Engineering, vol. 3099 (1997), pp. 238–247.*

* cited by examiner

Primary Examiner—Mark A. Robinson
Assistant Examiner—Alessandro Amari
(74) Attorney, Agent, or Firm—Jones Day (57) ABSTRACT

In at least part of the layers of the integrated optical channel waveguide system, such as cladding layers, a passive light guiding layer and an active light guiding layer, an adiabatic layer thickness transition positioned next to a working zone is used to adapt the waveguide structure in the working zones to individually optimized functionality. In this way, the relative layer thickness values as located in the working area, for example a sensor window, a modulation region and a fiber-chip region, can be individually optimized, for example, for maximal evanescent field sensitivity, for minimal modulation voltage and for efficient coupling of light power without the necessity of the optical layer-thickness values elsewhere in the system having to be adjusted. Incorporated in a Mach-Zehnder interferometer this results in an exceptionally sensitive and reliable sensor. Preferably the channel waveguide system is incorporated in an electronic circuitry in which e.g. a phase shift induced by the quantity to be determined is generated.

17 Claims, 5 Drawing Sheets

INTEGRATED OPTICAL WAVEGUIDE SYSTEM

BACKGROUND OF THE INVENTION

1. Field of the Invention

The present invention relates to an integrated optical channel waveguide system and, more particularly to a waveguide system with a substrate and a waveguide layer structure comprising a first cladding layer, a passive light guiding layer deposited on the first cladding layer, an electro-optical light guiding layer on the passive layer and a second cladding layer.

2. Description of the Related Art

An integrated optical channel waveguide system is known from the article "Fabrication and packaging of integrated chemo-optical sensors" published in the Journal "Sensors and Actuators B 1996, vol. 35–36, pages 234–240. In a system described there, optimization of, for example, the sensitivity of the system located in a working or active zone always influences the functioning of the channel system outside the working zone. In this way the optimization is only restrictedly feasible, which negatively influences the sensitivity of the total waveguide system It is remarked that besides the article cited above similar devices are disclosed in some further documents of which "Integrated optic adiabatic devices on silicon", published in IEEE Journal of Quantum Electronics, vol. 27 (1991) March no.3, pp. 556–566, discloses a possibility of adiabatically tapering waveguide sections for mode change in order to realise a coupler, a splitter, a multiplexer and a transformer.

The article "Integrated optics and new phenomena in optical waveguides", published in Reviews of Modern Physic, vol. 49, no.2. April 1977 pp.; 361–378 discloses a similar device with the aim for a better integration in optical circuitry with a large number of devices.

An article in Journal of Applied Physics, vol. 69 no. 1, June 1991 pp. 7425–7429 discloses an integrated double core layer waveguide structure wherein an upper core layer comprises an adiabatic transition zone in order to examine the difference between adiabatic and non-adiabatic transition of the guided light. This article thus teaches away from optimizing a device through adaption of at least part of the transitions of an integrated waveguide system to reach a sensitive device for sensing or modulation.

SUMMARY OF THE INVENTION

Because of the thickness reduction of the active light guiding layer beside the working zone, any influence on the channel system outside the working zone is avoided. As a result of the adapted adiabatic design of the layer-thickness reduction, loss of light power in this zone is also avoided or at least reduced. A simple and reproducible coupling between a light fibre supplying the light and/or a light fibre discharging the light and the optical channel system can also be realized. In the case of the preferred design, the light guiding layer comprises an electro-optic light guiding layer consisting of ZnO and a passive light of $Si_3N_4$ and the electro-optic light guiding layer exhibits an adiabatic layer-thickness reduction. Especially the adiabatic layer-thickness transition zone in the electro-optic light guiding layer reduces its layer-thickness outside the modulation working zone to at least almost zero.

Because the light guiding layer here is built up from an active and a passive layer, the layer-thickness reduction outside the active modulation zone can be performed without any restriction because there the passive light guiding layer will be responsible for the light guiding. Every negative influence on the channel system can therefore be avoided without restricting light-guiding throughout the channel system as such.

Conversely the passive light guiding layer can be provided with an adiabatic layer thickness transition zone such that the layer thickness located in the modulation working zone is eventually reduced to zero, and what is more, the space created in this way can be filled up by active light guiding material such as the already mentioned ZnO, by which its sensitivity to the applied voltage there can be further optimized.

In a preferential configuration the layer thickness of an existing $Si_3N_4$ passive light guiding layer located in a sensor window working zone, is optimized for sensing using the evanescent field tail of the light to be used. In particular the system is designed as a sensor for measuring chemical and/or physical quantities that influence the refraction-index profile probed by the evanescent field of the light used. Especially at this point in the measurement process, use is made of the evanescent field of the light employed and the sensitivity to the quantity to be measured can be increased by making the sensor windows longer, for example by removing the second cladding layer over a greater length. Consequently, no extra properties of the light used are required for enhancing the sensitivity.

In a further preferential embodiment, the layer thickness of at least one of the cladding layers present in the electro-optical modulation working zone is reduced, in such a way that the active voltage modulation sorts out maximal effects in the active light-guide material, without causing intensity loss of the light used due to an underlying electric conductive substrate material, and/or a locally introduced upper electrode. To obtain a window for the sensing process, the second cladding layer is also locally completely or at least almost removed down to the passive light guiding layer. Due to the fact that in these configurations the layer thickness of one or both of the cladding layers, which preferably consist of $SiO_2$, is reduced at the modulation working zone and similarly is decreased to at least almost zero at the sensor windows working zone, it is possible to optimize the functionality of the waveguide structure, so both optimal sensitivity for evanescent field sensing as well as minimal electric driving voltage modulation can be obtained, without the light confinement, as seen over the whole channel system, being reduced.

In a further preferential design the passive light guiding layer is provided with an adiabatic transition zone leading to a layer thickness, which at that location is optimally adjusted to the mode profile geometry of the light-supplying optic fibre. Especially the layer thickness values of both the passive light guiding layer and the first cladding layer are locally optimized to discriminate between TE and TM polarized light in such a way that the TE is optimally coupled in, and optimally transmitted as well, both with respect to the TM polarized light.

Optimal coupling can be realized with a minimum loss of light, without the structure of the channel set outside the zone needing to be adjusted, by adapting the layer thickness of the passive light guiding layer at the location where the light is coupled in. Discrimination between TE-polarized light and TM-polarized light and efficient TE-acceptation can be realized by a corresponding design of the geometry of the waveguide structure and of a transition zone in the passive waveguide guiding layer respectively, again also without the layer set-up outside that zone being further negatively influenced. Here, discrimination between TE and TM polarized light with the coupling of the light into the interferometer gives the substantial advantage that the whole interferometer measurement process can be carried out with only TE polarized light by which dispersion in the measuring light is reduced, and a significantly more unambiguous interferometer signal is generated.

In a further design a substrate preferentially made of Si is fitted with a V-shaped groove in order to realize a detachable and/or optically adjustable coupling of an optical input fibre and/or output fibre to the light guide channel system. A handy for use transit opening through which simply and with a high degree of precision the input and or output fibre can be inserted and positioned is obtained by attaching a part of the unused V-groove upside down on the V-groove already referred to.

Because of the exact dimensions of the V-groove in the Si, which can be very accurately obtained using etching techniques, the fibre placed there can give an optimal and good reproducible coupling of the light from the fiber into the layer in question of the channel system. As a result of the previously mentioned adiabatic thickness transition of the light guiding layer at this location, the thickness of the channel layer there can be optimally adjusted to the input and/or output fibre. Both properties together result into an optimal coupling with respect to reliability as well as to reduced loss of light. A light source equipped with an optical fibre (pigtailed), such as for example a gas laser or a solid-state (such as a diode laser) can therefore be reliably coupled to the channel system. Thereby a simple detachable coupling can be achieved, having the advantage that in the case of any technical failure, either the laser or the waveguide system can be replaced. On the other hand a permanent coupling can be realized in which case often the light loss or variation in the light loss can be further reduced.

In another preferential configuration, according to the invention, a light guiding system forms part of a Mach-Zehnder type interferometer. Especially such a Mach-Zehnder interferometer, including in both of its branches a sensor window as well as a modulator provided with electrodes, where one of the sensor windows is shielded against the influence of the quantity to be measured.

A Mach-Zehnder interferometer is known from U.S. Pat. No. 5,533,151 or U.S. Pat. No. 5,377,088 and always comprises two arms, where is one arm an external quantity introduces a phase change due to variations of the refractive index. This variation can be extremely accurately measured by comparing this light propagation with the light propagated through the reference arm which cannot be influenced by the measurand.

A practical design for a Mach-Zehnder interferometer according to the invention can be designed. This makes the interferometer less sensitive to external influences other than by the measurand. Especially if such an interferometer is incorporated in an electrical circuit for the derivation of the measurand induced phase shift from the situation at which the anti phase signals have identical intensities. Thus a signal is generated, that is even more unambiguous and more insensitive to external disturbances.

A practical design of an electrical circuit for that purpose is formulated herein. The electrical circuit is particularly equipped with a signal generator for activating a (couple of) modulation electrode(s) in the system, with a threshold-value switch for converting the modulated analogue output signal into a digital signal, and with a digital signal processor for an accurate determination of the value of the measurand from the modulated output signal.

BRIEF DESCRIPTION OF THE DRAWINGS

On basis of the drawings some preferential designs according to the invention will be described in the following text. For all figures holds that the layer thicknesses in the layer structure are optimized for a wavelength of 633 nm. The drawings show.

DETAILED DESCRIPTION OF THE PREFERRED EMBODIMENTS

Figure 1:
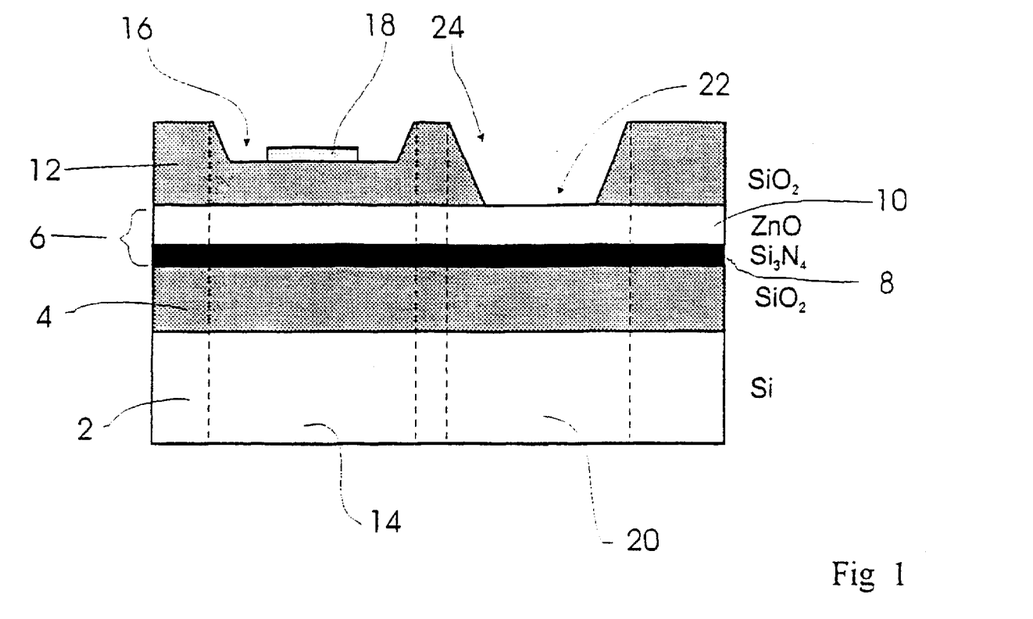
FIG. 1: a well-known integrated optical-channel waveguide system.

An integrated optic channel waveguide system as schematically represented in FIG. 1 comprises a light guiding structure on top of a substrate 2 preferably made of Si, and a first cladding layer 4 preferable made of $SiO_2$ having a thickness of about 500 nm, a light guiding layer 6, here being composed of a passive light-guiding layer 8, preferably of $Si_3N$, with a thickness, for example, about 20 nm, and preferably a ZnO electro-optical light guiding layer 10 with a thickness of about 500 nm, and a second cladding layer 12 preferably also consisting of $SiO_2$ with a thickness of about 500 nm. Here the system comprises a first working zone 14 with a modulation electrode 18 applied inside a recess 16 in the second enclosure layer, and a second working zone 20 with a sensor window 22, here also formed by a recess 24 in the second enclosure layer. This latter recess can reach the light guiding layer 6, as is shown in the figure. Such a layer system is suitable for sensing, utilizing The sensor window 22, as well as for electro-optical modulation using the modulation electrode 18.

Figure 2:
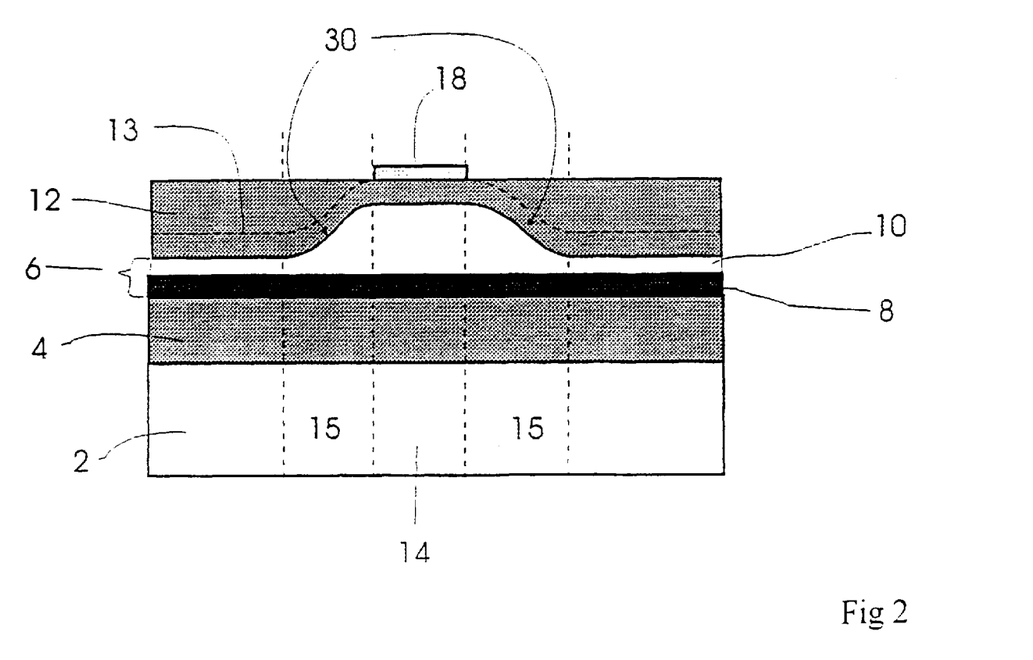
FIG. 2: a similar system in which, according to the invention, the electro-optical light guiding layer is provided with an adapted adiabatic layer-thickness transition zone.

In FIG. 2 the active electro-optical light guiding layer 10, which also here preferably consists of ZnO and has a layer thickness of for example 500 nm, beside a working zone 14, is provided with an adiabatic layer-thickness reduction 30 in a layer thickness transition zone 15 on both sides of the working zone 14. The layer stack here also contains a substrate 2, a first cladding layer 4, a passive light guiding layer 8 and an active light guiding layer 10 on top of which a second enclosure layer 12 is found, that either has a uniform thickness, as shown by the dashed line 13, or can continue as shown at the top right-hand side. On the second enclosure layer an electrode 18 is applied within the working zone. ZnO is especially suitable for electrical voltage modulation because this material both shows a high sensitivity to electrical voltage modulation, as well as an appropriate refractive index as a light guiding layer. The layer-thickness reduction can be taken so far that outside the adiabatic layer-thickness transition zone 15, no more ZnO is present and only the passive light guiding layer 8 takes care of the light guiding there. Preferable the layer-thickness transition zones begin at the edges of the working zone, which is also determined by the electrode 18.

Figure 3:
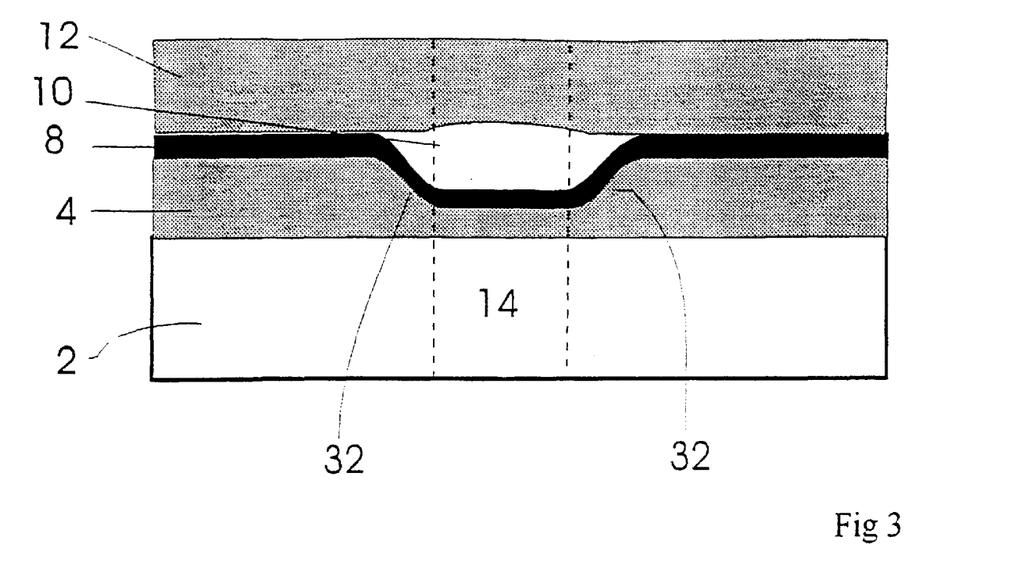
FIG. 3: a similar system in which, according to the invention, one of the cladding layers is provided with an adiabatic layer thickness transition zone.
Figure 4:
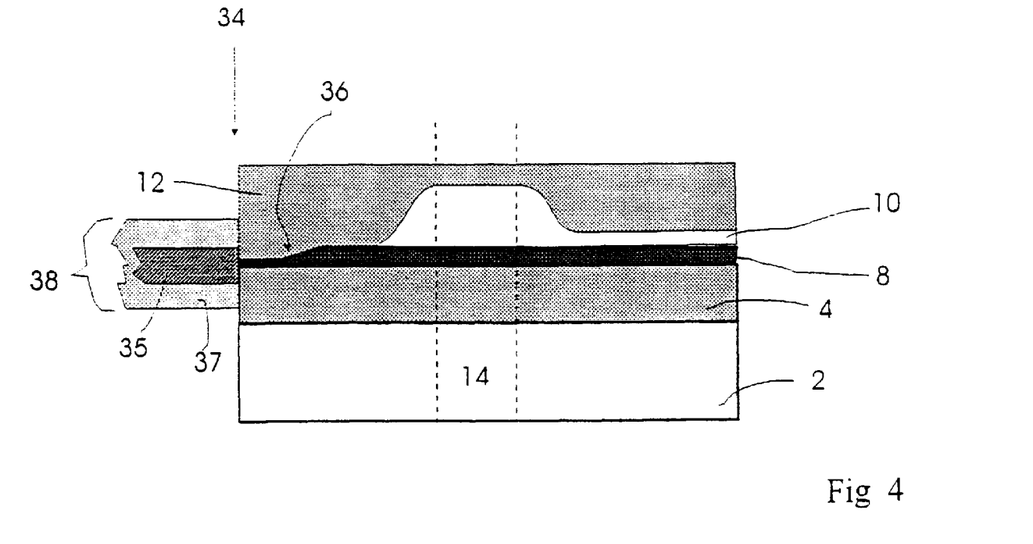
FIG. 4: a preferential design in which the passive light guiding layer on an output-side of the system is provided with an adiabatic layer adjustment.

A preferable design, as illustrated in FIG. 3, shows next to a first cladding layer 4 provided with adiabatic layer-thickness transition zones 32, a substrate 2, a passive light guiding layer 8, preferentially with a uniform thickness and an active light guiding layer 10 that is, as it were, fills up the space that is created by locally thinning the first cladding layer. It should be mentioned here that the geometry of an optical adiabatic layer-thickness transition zone for a light guiding layer such as ZnO layer is certainly not identical with the geometry of a similar adiabatic layer thickness transaction zone in an enclosure layer. The geometry, the slope profile and with that the length of the transition zone are, among other things dependent on the refractive index of the relevant layers and on the refractive index of neighbouring layers. Here the ZnO layer thickness can also reduce to zero as shown in FIG. 3, but that is not necessary. Otherwise this design form can be equipped with an active light guiding layer of uniform layer thickness or the passive light guiding layer can be provided with a suitable layer-thickness transition zone in order to contain the previously mentioned possible difference in the geometry. FIG. 4 shows a design form in which a passive light-conducting layer 8 at a light input side 34 is finished with an adiabatic layer-thickness transition zone 36, resulting in a layer thickness of about 10 nm. Using this layer-thickness adaptation, an optimal coupling with an input fibre 38 having a nucleus 35 and a cladding 37 can be realized. An optimal coupling, in this case, on the one hand includes a coupling with a minimum loss of light, but certainly also a coupling with an optimal discrimination between TE polarized and TM polarized light supplied from the input fibre. This effect is enlarged by choosing an optimal thickness for cladding layer 4. In this way the interferometer can work with only TE (or TM) polarized light by which measurement signals with a higher resolution are generated and the signal processing becomes simpler.

Figure 5:
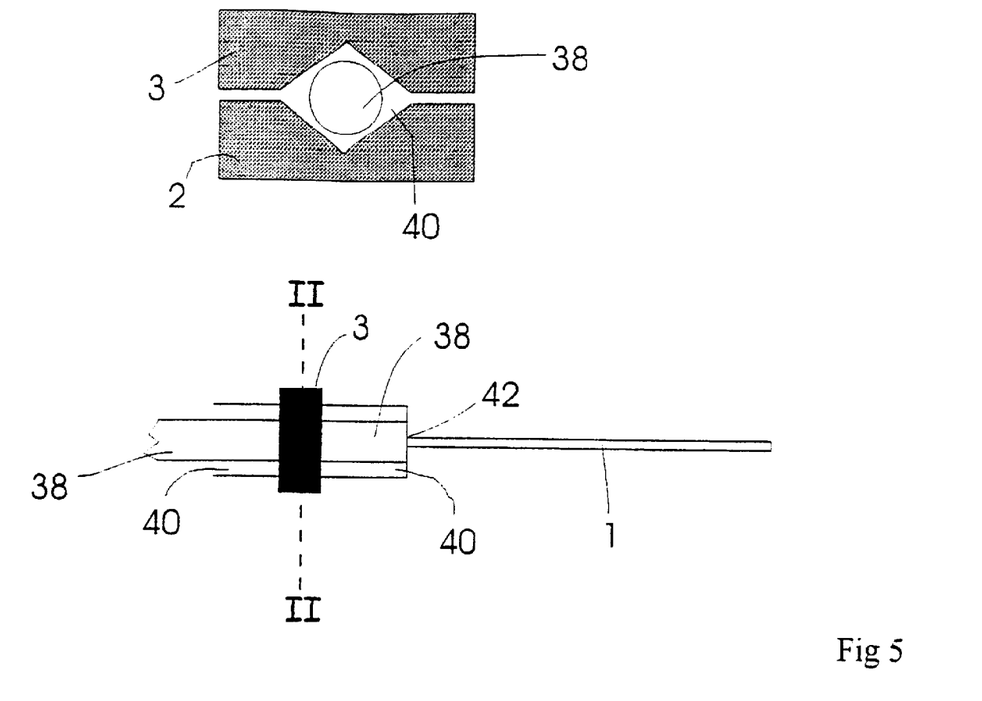
FIG. 5: a cross-section and a top view of the fibre-chip connector.

In FIG. 5 an example of a design is sketched of a fibre-to-waveguide channel system coupling showing respectively a cross-section and a top view of a fibre 38 encapsulated in a V-form 15 groove 40. The V-groove is made in a Si-substrate 2, and the fibre is permanently positioned and covered with another piece of the substrate 3, preferable being a part of the same V-groove that was first used. Then, if necessary, removable, but in general fixed fibre is optically connected at the input side 42 to the channel waveguide system 1.

Figure 6:
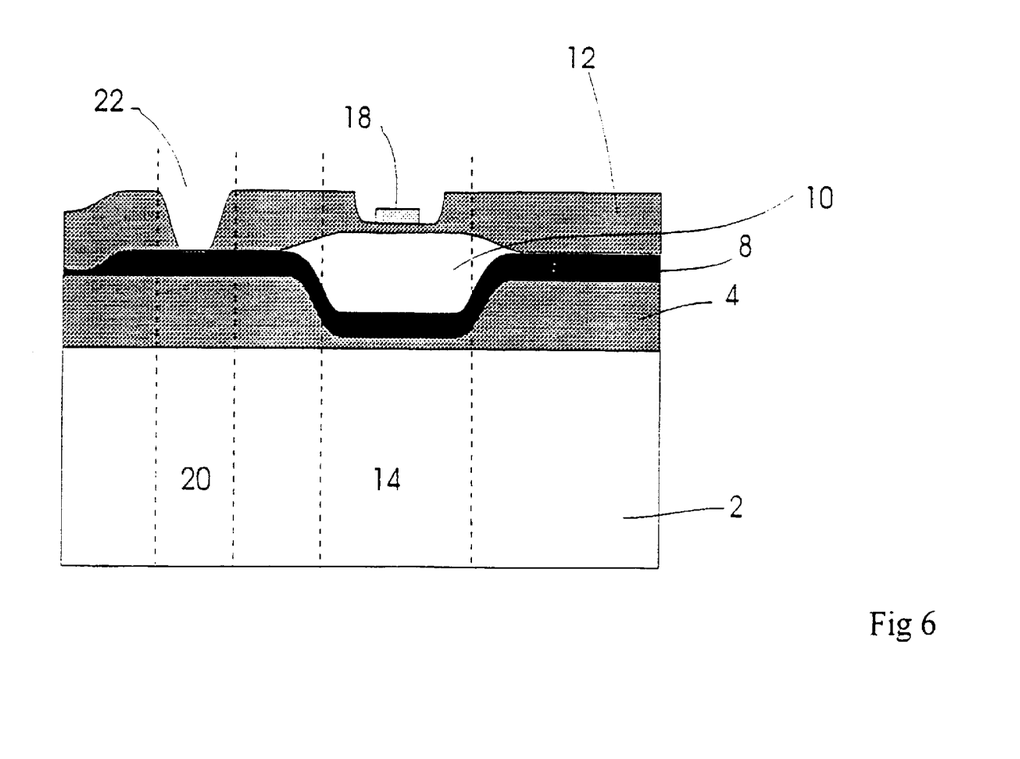
FIG. 6: a preferential design in which several layers show an adiabatic layer-thickness transition zone.

A preferential design is given in FIG. 6, in which the first passive light guiding layer 8 as well as the active light guiding layer 10 and both cladding layers 4 and 12 are provided with an adiabatic-layer thickness transition zone. All the advantages of each of the separate layer thickness transition zones are combined in this design and can be optimized independently from each other. If it would be advantageous an additional layer, for example a (chemical) separation or adhesion layer, can be applied between the layers already mentioned, for example between the passive and the active light guiding layers. In the illustrated design form there is a sensor window 22 as well as a modulation electrode 18 included. Such an integrated optical channel waveguide can, for example form part of a Mach-Zehnder interferometer system as shown in FIG. 7.

Figure 7:
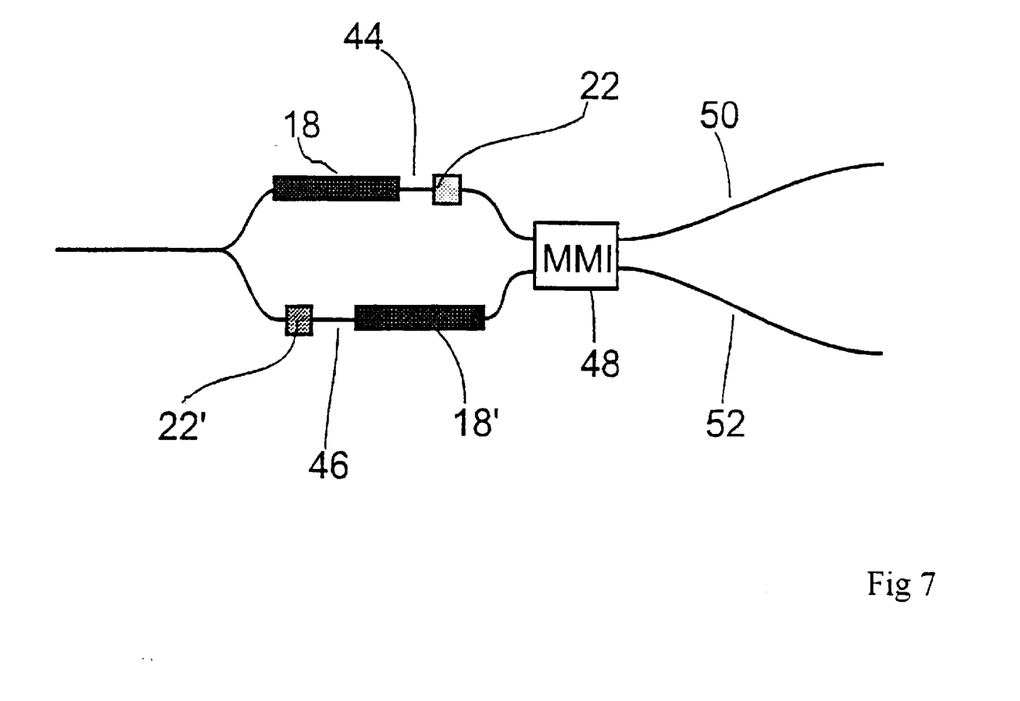
FIG. 7: a Mach-Zehnder type interferometer equipped with such a system.

A Mach-Zehnder interferometer as depicted in FIG. 7 is already well-known, for example, from the previously mentioned U.S. patents, and comprises a light-input device, for example an optical fibre, a measuring arm 44 and a reference arm 46 each fitted with a sensor window 22 respectively 22', as well as with an active zone, provided with an electrical voltage modulating electrode 18 respectively 18'. Both arms are connected to an optical power splitter or combiner, for example a Y-shaped junction or an multi-mode interferometer (MMI) 48 as is sketched here, with a first output 50 and a second output 52. Thus a nearly symmetrical system is realized by which its performance can be independent of external influences such as the surrounding temperature and similar causes. The sensor window 22' in the reference arm 46 is preferably shielded against the influence of the external variable to be measured, such as the relative humidity, the composition of gases and liquids, variations of the optical refractive index, temperature variations etc. Using such an interferometer two signals are generated that are, in principle, both influenced to the same extent, except for the phase shift induced by the quantity to be measured. Therefore the measurement is simple and shows a high accuracy.

In order to carry out the measurement, use can be made of laser light that directly or by means of an input fibre can be coupled in. As already mentioned it is possible, according to the invention, when coupling in, to select TE polarized light. With the above mentioned adiabatic layer thickness adaptation zone of the light guiding layer and the likewise previously mentioned accurate optical input coupling, the interferometer is exceptionally sensitive.

Figure 8:
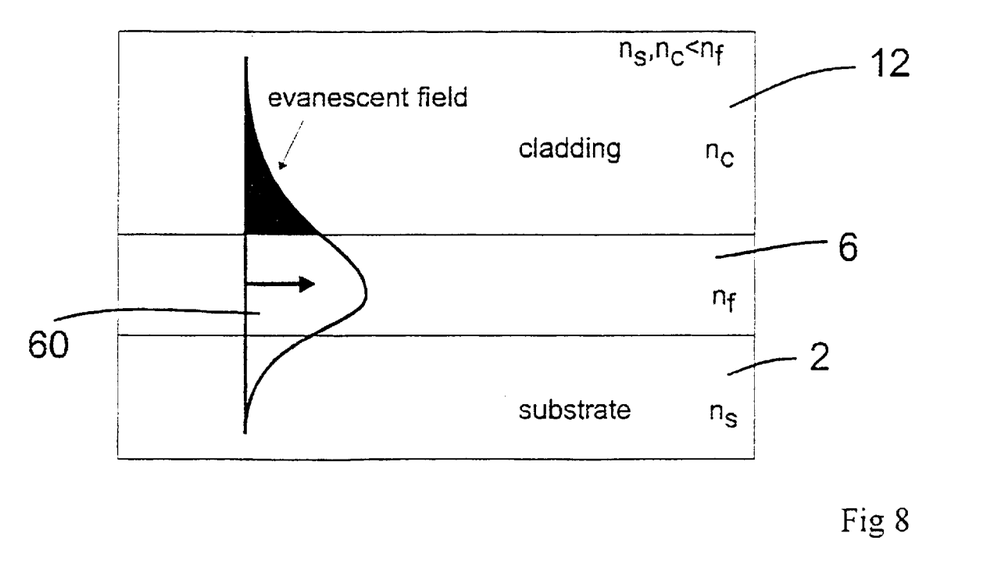
FIG. 8: a cross-section of a waveguide structure in which is shown the evanescent field of the light on which the sensor is based.

Measurements with such an interferometer would usually be carried out with the input light propagating confined in and around the guiding layer. Using the adiabatic layer-thickness application it is possible, according to the invention to perform measurements with the help of the so-called evanescent tail of the used light. In order to clarify this, FIG. 8 shows how the propagation of the light in the waveguide channel system is divided into a central part 60 inside the light guiding layer 6 and an evanescent field 62 present in an cladding layer 12. Reducing the layer thickness of the cladding layer 12 by means of an adiabatic layer-thickness zone down to zero, the evanescent field here shows a high sensitivity to external influences and in this way a window for sensing is formed. Because the power ratio between the central part 60 and the evanescent tail 62 is dependent on the layer thickness of the light guiding layer 6, it is possible to obtain, in the sensor window, a larger part of the light in the evanescent tail and thus an even higher sensitivity for external influences, by means of a for example preceding adiabatic layer-thickness transition zone of the light guiding layer 6.

Figure 9:
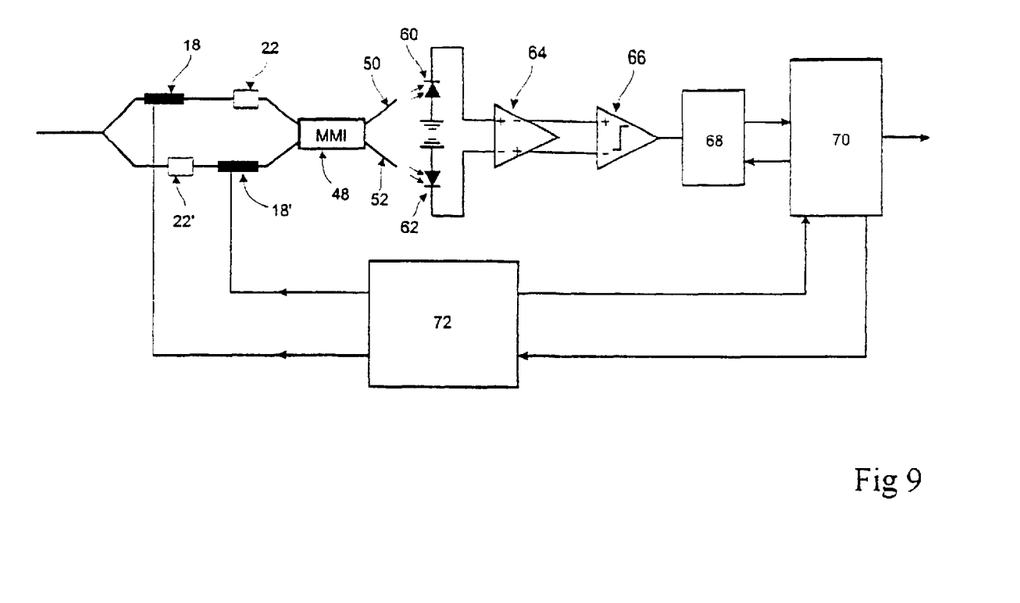
FIG. 9: an electronic circuit diagram for the detection of interferometer output signals.

FIG. 9 depicts a functional diagram of an electrical circuit with which the phase shift imposed by the measuring quantity can be derived from the output signals to the Mach-Zehnder interferometer. The generated optical output signals from the output channels 50 and 52 are first converted into electrical signals by means of photo detectors 61 and 63 and subsequently amplified by the preamplifier 64. Afterwards, using the threshold value switch 66, detection takes place at the point at which the anti phased output signals, have identical intensities. The advantage of this method of detection is that it is not interfered with by common fluctuations of the light power from both of the output channels 50 and 52, regardless of the origin of these fluctuations. Besides this, the sensitivity of the detection for the imposed phase shift is maximal in the previously mentioned detection point. In order to make unambiguous detection possible, during a measurement cycle a time-periodic phase shift is applied with the help of a phase modulator 18, for example one such as mentioned previously. Depending on the specific design form, one or more detection points can be obtained during the measurement cycle. The time dependence of this time periodic phase shift is linear, and is realized by applying an electric voltage with the same dependence to the phase modulator. In the preferential design in FIG. 7 such a voltage but with a mutually opposite polarity is applied to both electrodes 18 and 18'. An electrical waveform generator 68 takes care of generating and making available the mentioned voltage(s). The peak-peak value of the generated voltage waveform is adjusted by a digital signal processing and control unit 70 in such a way that during every measuring cycle the previously mentioned detection point is passed at least once. The time interval between the start of the measurement cycle and the passing of the detection point is an unambiguous and linear measure for the phase shift imposed by the measurand, and by measuring this time the phase shift can be obtained. The sampling of the detection point is quickly completed because the threshold-value switch 66 directly converts the passing of the detection point into a steep slope of a binary signal and with that, the pulse duration of this binary signal is established. The pulse-duration coding makes a simple and highly linear quantification possible by means of a digital time-interval counter 68. A digital processing and control unit 70 carries out the reconstruction of the measurand induced phase shift on the basis of the quantified sampling times, and delivers a digital output signal. The digital signed processing and control unit 70 is also responsible for the synchronization of the waveform generation 72 with the time-interval counter 68. The digital signal processing and control unit 70 can also optionally carry out a further final processing of the reconstructed phase shift in order, for example, to increase the measurement accuracy.

What is claimed is:

1. Integrated optical channel waveguide system with a substrate (2) carrying a waveguide layer structure, comprising in succession a first cladding layer (4), a passive light guiding layer (8), an electro-optical light guiding layer (10) and a second cladding layer (12), characterized in that at least said passive light guiding layer and said electro-optical light guiding layer and said second cladding layer are provided along a longitudinal direction of the waveguide layer structure with an adiabatic transition zone (15, 24, 32, 36) formed by a continuous variation in the layer thickness in said direction, these layer thickness variations thereby enabling a mutually independent optimizing of each predetermined optical function within a combination of functions to be used in the waveguide layer structure.

2. Integrated optical channel waveguide system as claimed in claim 1 characterized in that at the adiabatic layer thickness transition zone (15, 32) in the electro-optical light guiding layer (10) the layer thickness of said layer is reduced to zero.

3. Integrated optical channel waveguide system as claimed in claim 2 characterized in that the layer thickness of at least one of the two cladding layers is at the location of an electro-optical modulation zone (14) reduced to generate a maximum effect in the active waveguide material upon a voltage modulation without suffering loss caused by an underlying electrical conducting carrier material or a locally introduced upper electrode.

4. Integrated optical channel waveguide system as claimed in claim 2 characterized in that the second cladding layer (12) is locally removed to at least almost onto the passive guiding layer (8) at a local adiabatic layer thickness transition (24) defining a window (22) for sensing a chemical and/or physical quantity which influences the refractive index profile in the evanescent field region at the sensing window location.

5. Integrated optical channel waveguide system as claimed in claim 1 characterized in that the layer thickness of at least one of the two cladding layers is at the location of an electro-optical modulation zone (14) reduced to generate a maximum effect in the active waveguide material upon a voltage modulation without suffering loss caused by an underlying electrical conducting carrier material or a locally introduced upper electrode.

6. Integrated optical channel waveguide system as claimed in claim 5 characterized in that the second cladding layer (12) is locally removed to at least almost onto the passive guiding layer (8) at a local adiabatic layer, thickness transition (24) defining a window (22) for sensing a chemical and/or physical quantity which influences the refractive index profile in the evanescent field region at the sensing window location.

7. Integrated optical channel waveguide system as claimed in claim 1 characterized in that the second cladding layer (12) is locally removed to at least almost onto the passive guiding layer (8) at a local adiabatic layer thickness transition (24) defining a window (22) for sensing a chemical and/or physical quantity which influences the refractive index profile in the evanescent field region at the sensing window location.

8. Integrated optical channel waveguide system as claimed in claim 7 characterized in that the passive light guiding layer (8) is provided with an adiabatic layer thickness transition (36) optimizing light acceptance for transverse electric polarized light, and the layer thickness of the first cladding layer (4) is arranged to optimize light transmission of transverse electric polarized light with respect to transverse magnetic polarized light.

9. Integrated optical channel waveguide system as claimed in claim 1 characterized in that the passive light guiding layer (8) is provided with an adiabatic layer thickness transition (36) optimizing light acceptance for transverse electric polarized light, and the layer thickness of the first cladding layer (4) is arranged to optimize light transmission of transverse electric polarized light with respect to transverse magnetic polarized light.

10. Integrated optical channel waveguide system as claimed in claim 9 including a circuit having a measuring arm (44) and a reference arm (46) and a Mach-Zehnder type interferometer (48) as well as sensor windows (22, 22') and electrodes (18, 18'), whereby one of the sensor windows is arranged as a reference window and is shielded against the quantity to be measured.

11. Integrated optical channel waveguide system as claimed in claim 10, characterized in that two counter-phased control signals are used to modulate two electro-optical modulation zones of the Mach-Zehnder interferometer, the substrate layer (2) being arranged as ground electrode for the modulating signals.

12. Integrated optical channel waveguide system as claimed in claim 11, characterized in that the waveguide system is incorporated in an electrical circuit delivering a phase shift induced by a quantity to be measured relative to a reference point at which electro-optical phase modulation signals of an interferometer output show maximal sensitivity.

13. Integrated optical channel waveguide system as claimed in claim 12, characterized in that the system is equipped with a signal generator for feeding an electrode structure on top of an electro-optical light guiding material, a threshold value switch for transforming an analogue modulated relative measuring signal into a digital signal of which a modulated pulse duration is unambiguously dependant on the quantity to be measured and with a digital signal processor or accurately determining a quantity to be measured from the modulated pulse duration.

14. Integrated optical channel waveguide system as claimed in claim 1 including a circuit having a measuring arm (44) and a reference arm (46) and a Mach-Zehnder type interferometer (48) as well as sensor windows (22, 22') and electrodes (18, 18'), whereby one of the sensor windows is arranged as a reference window and is shielded against the quantity to be measured.

15. Integrated optical channel waveguide system as claimed in claim 14, characterized in that two counter-phased control signals are used to modulate two electro-optical modulation zones of the Mach-Zehnder interferometer, the substrate layer (2) being arranged as ground electrode for the modulating signals.

16. Integrated optical channel waveguide system as claimed in claim 15, characterized in that the waveguide system is incorporated in an electrical circuit delivering a phase shift induced by a quantity to be measured relative to a reference point at which electro-optical phase modulation signals of an interferometer output show maximal sensitivity.

17. Integrated optical channel waveguide system as claimed in claim 16, characterized in that the system is equipped with a signal generator for feeding an electrode structure on top of an electro-optical light guiding material, a threshold value switch for transforming an analogue modulated relative measuring signal into a digital signal of which a modulated pulse duration is unambiguously dependant on the quantity to be measured and with a digital signal processor or accurately determining a quantity to be measured from the modulated pulse duration.

* * * * *